(12) United States Patent
Simon

(10) Patent No.: US 11,707,130 B2
(45) Date of Patent: Jul. 25, 2023

(54) FLUID-FILLED CLEANING HEAD

(71) Applicant: L'Oreal, Paris (FR)

(72) Inventor: Danny Elery Simon, Redmond, WA (US)

(73) Assignee: L'Oreal, Paris (FR)

( * ) Notice: Subject to any disclaimer, the term of this patent is extended or adjusted under 35 U.S.C. 154(b) by 277 days.

(21) Appl. No.: 17/135,857

(22) Filed: Dec. 28, 2020

(65) Prior Publication Data

US 2021/0196035 A1    Jul. 1, 2021

Related U.S. Application Data

(60) Provisional application No. 62/953,855, filed on Dec. 26, 2019.

(51) Int. Cl.
| | | |
|---|---|---|
| *A47K 7/04* | (2006.01) | |
| *A46B 9/00* | (2006.01) | |
| *A46B 7/04* | (2006.01) | |
| *A46B 13/02* | (2006.01) | |
| *A61B 17/54* | (2006.01) | |

(52) U.S. Cl.
CPC ............... *A46B 9/005* (2013.01); *A46B 7/04* (2013.01); *A46B 13/02* (2013.01); *A47K 7/04* (2013.01); *A46B 2200/1006* (2013.01); *A61B 17/54* (2013.01)

(58) Field of Classification Search
CPC .................................. A46B 9/00; A46B 13/02
See application file for complete search history.

(56) References Cited

U.S. PATENT DOCUMENTS

| | | |
|---|---|---|
| 1,772,501 A | 8/1930 | Shelton |
| 3,103,679 A | 9/1963 | Clemens |
| 3,196,299 A | 7/1965 | Kott |
| 3,542,519 A | 11/1970 | Montalto |
| 3,605,347 A | 9/1971 | Barry |
| 3,699,952 A | 10/1972 | Waters |
| 4,014,064 A | 3/1977 | Okazaki |
| 4,161,050 A | 7/1979 | Sasaki et al. |
| 4,325,392 A | 4/1982 | Item et al. |
| 4,475,261 A | 10/1984 | Okumura et al. |
| 4,655,232 A | 4/1987 | Ficke |

(Continued)

FOREIGN PATENT DOCUMENTS

| | | |
|---|---|---|
| GB | 2 323 026 A | 9/1998 |
| JP | H1-185202 A | 7/1989 |

(Continued)

*Primary Examiner* — Michael D Jennings
(74) *Attorney, Agent, or Firm* — Christensen O'Connor Johnson Kindness PLLC

(57) ABSTRACT

A cleaning head for a personal care appliance includes an elastic bladder having a bladder wall enclosing a fluid. The bladder wall has an inner base portion with a base thickness, which may be non-uniform, and a plurality of spaced projections extending outwardly from the inner base portion. The bladder is fixedly attached to a receiver portion of a bladder support, and a retainer is provided for attaching the bladder support to the personal care appliance such that the bladder support is drivably engaged by the personal care appliance. At least some of the plurality of spaced projections are configured to dynamically engage and disengage with neighboring ones of the plurality of spaced projections during use.

20 Claims, 8 Drawing Sheets

(56) References Cited

U.S. PATENT DOCUMENTS

| | | |
|---|---|---|
| 4,722,111 A | 2/1988 | Brodey et al. |
| 4,802,255 A | 2/1989 | Breuer |
| 4,858,600 A | 8/1989 | Gross |
| 5,062,209 A | 11/1991 | Rais |
| 5,313,909 A | 5/1994 | Tseng et al. |
| 5,322,031 A | 6/1994 | Lerner |
| 5,388,331 A | 2/1995 | Doroodian-Shoja Siamak |
| 5,416,942 A | 5/1995 | Baldacci |
| 5,500,975 A | 3/1996 | Sano |
| 5,652,990 A | 8/1997 | Driesen et al. |
| 5,860,183 A | 1/1999 | Kam |
| 5,891,063 A | 4/1999 | Vigil |
| 5,906,834 A | 5/1999 | Tseng |
| 5,998,431 A | 12/1999 | Tseng |
| 6,020,425 A | 2/2000 | Wang |
| 6,058,541 A | 5/2000 | Masterman et al. |
| 6,295,733 B1 | 10/2001 | Wexler |
| 6,373,786 B1 | 4/2002 | Kagan |
| 6,412,139 B1 | 7/2002 | Weihrauch |
| 6,482,511 B1 | 11/2002 | Martinez-Antonio |
| 6,546,586 B2 | 4/2003 | Cho |
| 6,604,531 B2 | 8/2003 | Nakamura et al. |
| 7,338,664 B2 | 3/2008 | Tseng |
| 7,547,737 B2 | 6/2009 | Kochvar |
| 7,695,207 B1 | 4/2010 | Laghi |
| 7,786,626 B2 | 8/2010 | Reishus et al. |
| 8,448,286 B2 | 5/2013 | Driesen et al. |
| 9,750,533 B2 | 9/2017 | Brewer et al. |
| 9,788,693 B1 | 10/2017 | Zhou |
| 2002/0049399 A1 | 4/2002 | Stempf |
| 2002/0088068 A1 | 7/2002 | Levy et al. |
| 2002/0138926 A1 | 10/2002 | Brown, Jr. et al. |
| 2003/0035953 A1 | 2/2003 | Weihrauch |
| 2003/0077107 A1 | 4/2003 | Kuo |
| 2004/0103492 A1 | 6/2004 | Kwon et al. |
| 2004/0134010 A1 | 7/2004 | Tseng |
| 2004/0147984 A1 | 7/2004 | Altshuler |
| 2004/0249322 A1 | 12/2004 | Cohen |
| 2005/0277950 A1 | 12/2005 | Pilcher et al. |
| 2006/0100558 A1 | 5/2006 | Smith |
| 2006/0282963 A1 | 12/2006 | Brown et al. |
| 2007/0101530 A1 | 5/2007 | Furumoto |
| 2007/0206986 A1 | 9/2007 | Gueret |
| 2007/0207440 A1 | 9/2007 | Chen |
| 2008/0313835 A1 | 12/2008 | Russell et al. |
| 2009/0163984 A1 | 6/2009 | Robinson et al. |
| 2009/0177125 A1 | 7/2009 | Pilcher et al. |
| 2009/0222072 A1 | 9/2009 | Robinson et al. |
| 2010/0223745 A1 | 9/2010 | Kraemer et al. |
| 2011/0040235 A1 | 2/2011 | Castel |
| 2011/0200381 A1 | 8/2011 | Bylsma et al. |
| 2011/0220634 A1 | 9/2011 | Yeh |
| 2012/0301210 A1 | 11/2012 | Sturgis et al. |
| 2013/0007969 A1 | 1/2013 | Driesen et al. |
| 2013/0085556 A1 | 4/2013 | Gillespie et al. |
| 2014/0082866 A1 | 3/2014 | Fishcher et al. |
| 2014/0194900 A1 | 7/2014 | Sedic |
| 2014/0202493 A1 | 7/2014 | Zelickson et al. |
| 2014/0261380 A1 | 9/2014 | Rademacher et al. |
| 2014/0276255 A1 | 9/2014 | McGushion |
| 2014/0373871 A1 | 12/2014 | Chang |
| 2015/0182290 A1 | 7/2015 | Grez |
| 2015/0189980 A1 | 7/2015 | Hwang et al. |
| 2015/0297393 A1 | 10/2015 | McGushion |
| 2015/0333609 A1* | 11/2015 | Lattanzi .......... H02K 1/34 310/38 |
| 2015/0359324 A1 | 12/2015 | Brewer |
| 2016/0183671 A1 | 6/2016 | Skidmore |
| 2016/0184162 A1 | 6/2016 | Grez |
| 2016/0184173 A1 | 6/2016 | Chen |
| 2016/0206087 A1 | 7/2016 | Skidmore |
| 2016/0331106 A1 | 11/2016 | Khormaei |
| 2017/0086627 A1* | 3/2017 | Fang .................. A47K 7/043 |
| 2017/0189670 A1 | 7/2017 | Brunson |
| 2017/0367471 A1 | 12/2017 | Straka et al. |
| 2017/0367543 A1* | 12/2017 | Straka .................. A61H 7/005 |
| 2018/0092449 A1* | 4/2018 | Straka .................. A61H 7/004 |
| 2018/0295980 A1 | 10/2018 | Boersma |
| 2018/0317640 A1 | 11/2018 | Schar et al. |
| 2018/0352934 A1 | 12/2018 | Nasu |
| 2019/0029411 A1 | 1/2019 | Brewer et al. |
| 2019/0142147 A1* | 5/2019 | Quinn .................. A46B 11/066 4/606 |
| 2020/0170399 A1* | 6/2020 | Truong .............. A46B 13/003 |
| 2020/0237085 A1 | 7/2020 | Miller et al. |
| 2020/0253811 A1 | 8/2020 | Alexander |
| 2020/0352317 A1 | 11/2020 | Yeates et al. |

FOREIGN PATENT DOCUMENTS

| | | |
|---|---|---|
| JP | H7-250711 A | 10/1995 |
| JP | H9-299148 A | 11/1997 |
| JP | H10-225324 A | 8/1998 |
| JP | 2000-279230 A | 10/2000 |
| JP | 2003-245131 A | 9/2003 |
| JP | 2009-240768 A | 10/2009 |
| JP | 2009240768 | 10/2009 |
| WO | 93/03649 A1 | 3/1993 |
| WO | 01/56529 A2 | 8/2001 |
| WO | 2004/002267 A1 | 1/2004 |
| WO | 2005/092145 A2 | 10/2005 |
| WO | 2006/137028 A1 | 12/2006 |
| WO | 2009/084637 A1 | 7/2009 |
| WO | 2012/125370 A1 | 9/2012 |
| WO | 2013/191389 A1 | 12/2013 |
| WO | 2017064104 A1 | 4/2017 |
| WO | 2017102897 A1 | 6/2017 |
| WO | 2018152068 A1 | 8/2018 |

* cited by examiner

FLUID-FILLED CLEANING HEAD

CROSS-REFERENCE TO RELATED APPLICATION

This application claims the benefit of Provisional Application No. 62/953,855, filed Dec. 26, 2019; the entire disclosure of said application is hereby incorporated by reference herein.

BACKGROUND

Handheld personal care appliances used to care for, clean, or otherwise treat the skin or hair (e.g., to clean, massage and/or apply creams, cleansing solutions, or other substances to the skin or hair) are known and have gained increasing popularity. Such devices are most often used to provide daily hygienic skin care, in particular care for the facial skin. These devices usually include a small handheld casing having an internal motor and a self-contained power source (such as a battery) for producing a particular movement/action of a workpiece (e.g., a brush or pad), which in turn produces desired functional results. Examples of such appliances include power skin brushes and power toothbrushes, among others. Such personal care appliances have motor arrangements which produce either rotational movement or oscillating (back and forth) movement. For example, U.S. Patent Application Publication No. 2015/0333609 A1, to Lattanzi et al., which is hereby incorporated by reference in its entirety, discloses an oscillating motor for a personal care appliance. These devices typically include replaceable brush heads having a plurality of elongate bristles, typically tufts of bristles, that are fixed to a base element that is driven to oscillate or rotate. The brush heads are pressed or positioned against a user's skin and activated while moving the brush head over the desired dermal region to provide a cleansing action to remove dirt, makeup, and/or dead skin, and the like.

Some oscillating heads for handheld personal care appliances are known that have a working face having abrasive exfoliating heads, for treating rough skin conditions such as calluses or corns. For example, U.S. Pat. No. 9,750,533, to Brewer et al., which is hereby incorporated by reference in its entirety, discloses an exfoliating head for a personal care appliance.

While many such devices are known, there is room for improvement in the field of personal care appliances such as handheld skin and hair treatment devices. For example, it is desirable to have a cleaning head for a personal care appliance with improved effectiveness in cleaning, massaging, and gently removing materials from a user's skin.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A cleaning head for a personal care appliance includes an elastic bladder having a bladder wall enclosing a fluid. The bladder wall has an inner base portion with a base thickness, which may be non-uniform, and a plurality of spaced projections extending outwardly from the inner base portion. The bladder is fixedly attached to a receiver portion of a bladder support, and a retainer is provided for attaching the bladder support to the personal care appliance such that the bladder support is drivably engaged by the personal care appliance. At least some of the plurality of spaced projections are configured to dynamically engage and disengage with neighboring ones of the plurality of spaced projections during use.

In an embodiment the receiver portion of the bladder support comprises an annular wall configured to surround at least a portion of the elastic bladder.

In an embodiment the plurality of spaced projections have a polygonal cross section, for example, a square cross section.

In an embodiment the plurality of spaced projections have a transverse dimension between 0.060 inch and 0.125 inch.

In an embodiment the plurality of spaced projections have a nominal spacing in the range of 0.030 and 0.040 inch between adjacent spaced projections.

In an embodiment the elastic bladder comprises a natural or synthetic rubber.

In an embodiment the base thickness of the inner base portion is not constant.

In an embodiment the fluid in the elastic bladder comprises air.

In an embodiment the fluid in the elastic bladder comprises an oil or water.

In an embodiment the fluid in the elastic bladder is pressurized above atmospheric pressure.

In an embodiment the fluid in the elastic bladder is pressurized to at least 30 psia.

In an embodiment the elastic bladder comprises a relatively smaller diameter portion that engages the bladder support, and a relatively larger diameter portion extending from the smaller diameter portion.

In an embodiment the larger diameter portion defines a narrow circumferential surface, and wherein at least a portion of the plurality of spaced projections extend outwardly from the narrow circumferential surface.

In an embodiment the bladder support defines a cavity configured to receive the smaller diameter portion of the elastic bladder, and the larger diameter portion of the elastic bladder extends radially away from the bladder support.

In an embodiment the larger diameter portion of the elastic bladder extends radially beyond a radially outer edge of the retainer.

A personal care appliance with a cleaning head is disclosed, wherein the personal care appliance is configured to releasable and drivably engage a cleaning head as described above.

A cleaning head for a personal care appliance includes a bladder support comprising a receiver portion defining a cavity, an elastic bladder having a first portion disposed in the cavity and fixedly attached to the bladder support and a second portion having a non-uniform thickness and a plurality of spaced projections extending outwardly from the second portion, wherein the elastic bladder encloses a liquid; and a retainer configured to releasably attach the bladder support to the personal care appliance such that the bladder support is drivably engaged by the personal care appliance, wherein the elastic bladder is configured to flex during use such that the plurality of spaced projections engage and disengage with neighboring ones of the plurality of spaced projections during use.

In an embodiment the plurality of spaced projections have a polygonal cross section and have a nominal spacing in the range of 0.030 and 0.040 inch between adjacent spaced projections.

In an embodiment the first portion of the elastic bladder has a smaller transverse dimension than the second portion of the elastic bladder.

In an embodiment at least some of the plurality of spaced projections extend radially outwardly from the second portion of the elastic bladder.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The following disclosure provides examples of cleaning heads for a personal care appliance, and a personal care appliance configured to use the disclosed cleaning heads for cleaning and/or treating a user's skin. Personal care appliances and cleaning heads may be configured for deep cleaning, smoothing, exfoliating, and/or massaging the skin. The appliance and cleaning heads may be suitable for use on any area of a body. Cleaning heads in accordance with the present disclosure include a pliable fluid-filled bladder having a micro-engineered outer surface that is configured to facilitate skin cleaning, dead skin cell removal, or the like. It is contemplated that the cleaning heads may further include additional known components such as bristles, abrasive sections, and the like.

In some examples the personal care appliance oscillates the cleaning head during use, for example with rotational (i.e., clockwise/counterclockwise) oscillations, and may advantageously be used with a prior application of skin care formula. The oscillating action of the cleaning head may be rotational and/or translational oscillations. Typically, the personal care appliance drives the cleaning head in a periodic motion while the user positions the cleaning head against the user's skin, and/or moves the cleaning head over a region of the user's skin, to clean the desired dermal region. In some embodiments, the cleaning head may be configured to additionally treat rough skin conditions such as calluses, corns, or the like, by further including abrasive elements over a portion of an outer surface of the bladder.

In the following description certain details are described to provide a thorough understanding of one or more contemplated embodiments of the present invention. It will be apparent to persons skilled in the art that embodiments of the present disclosure may be practiced without all of the specific features or details described herein. In some instances well-known features or process steps are not described in detail to avoid unnecessarily obscuring novel aspects of the present disclosure. Further, it will be apparent to persons of skill in the art that embodiments of the present disclosure may employ any combination of features described herein.

Figure 1:
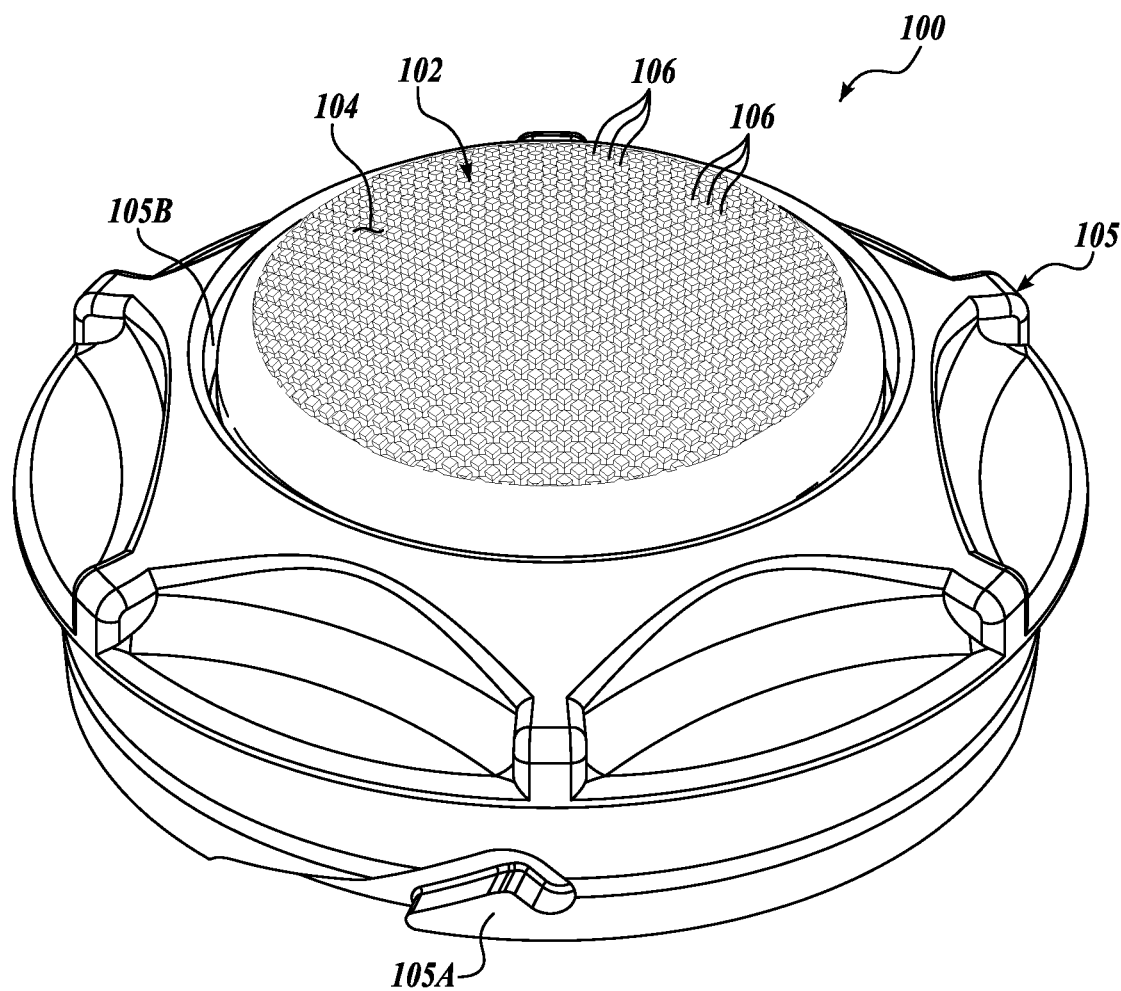
FIG. 1 is a perspective view of a cleaning head in accordance with the present invention.
Figure 2:
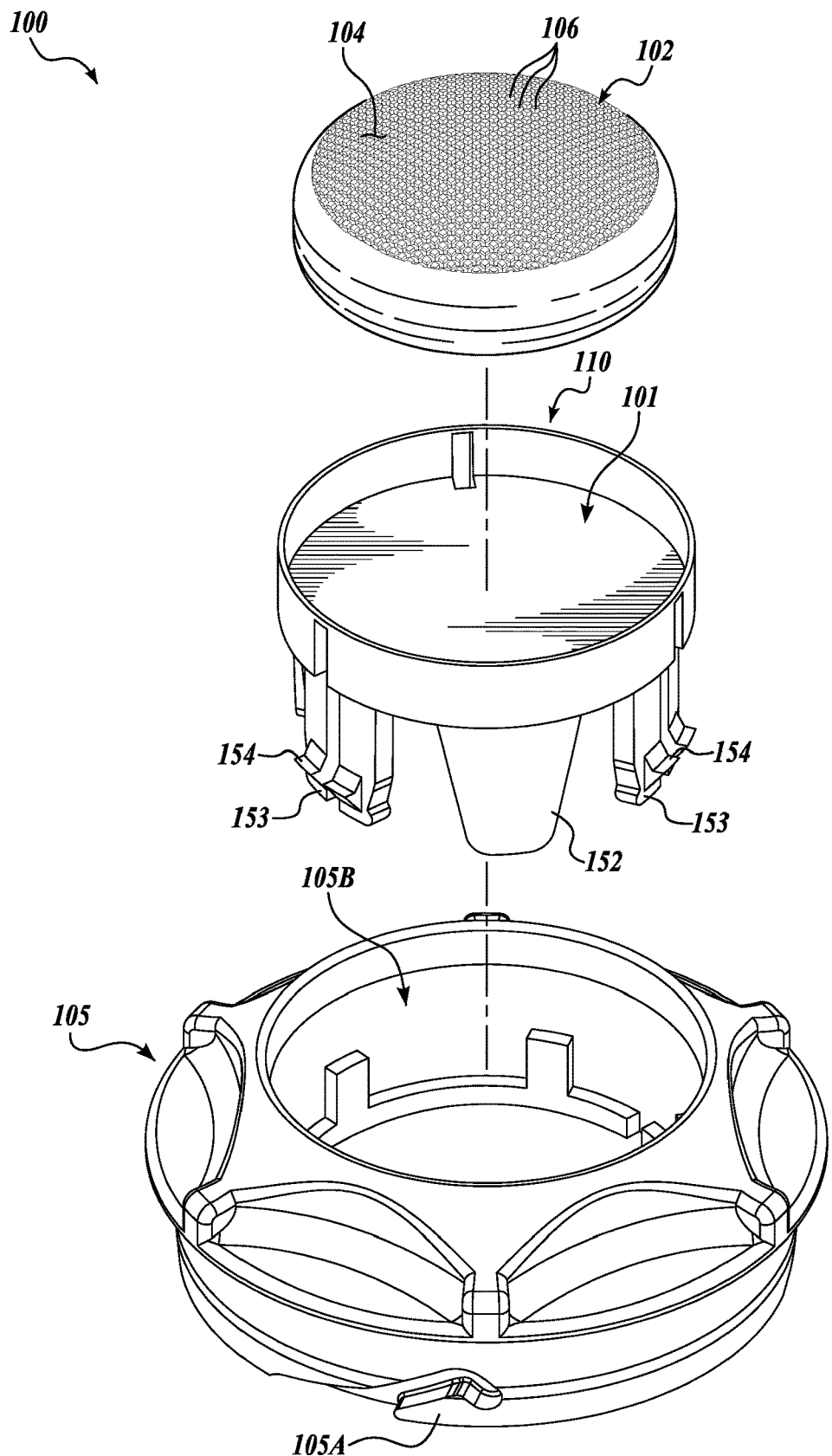
FIG. 2 is an exploded view of the cleaning head shown in FIG. 1.
Figure 3:
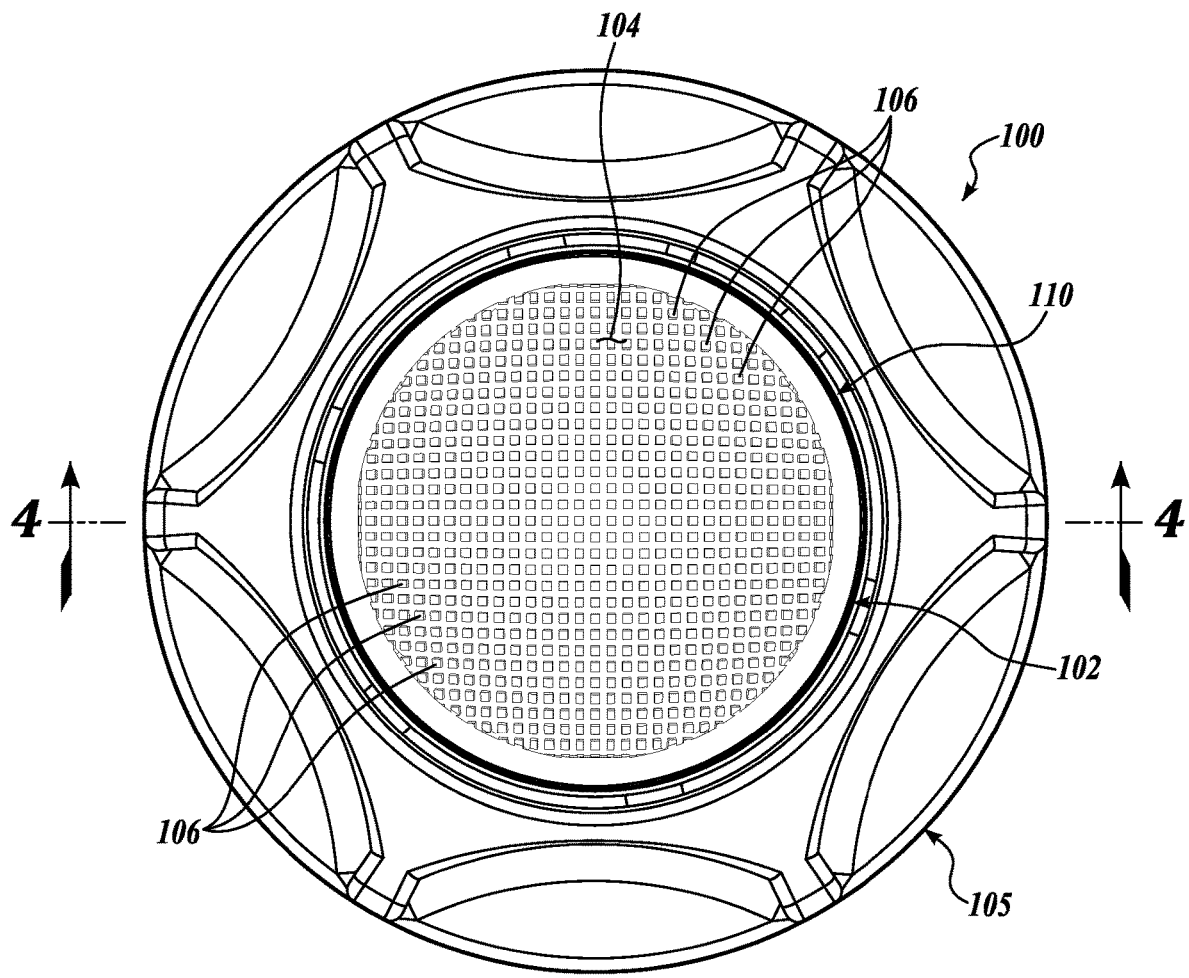
FIG. 3 is a top plan view of the cleaning head shown in FIG. 1.

FIG. 1 is a perspective view of a cleaning head 100 for a personal care appliance 22 (see FIG. 6) in accordance with the present disclosure. FIG. 2 shows an exploded view of the cleaning head 100, and FIG. 3 shows a top plan view of the cleaning head 100.

Figure 6:
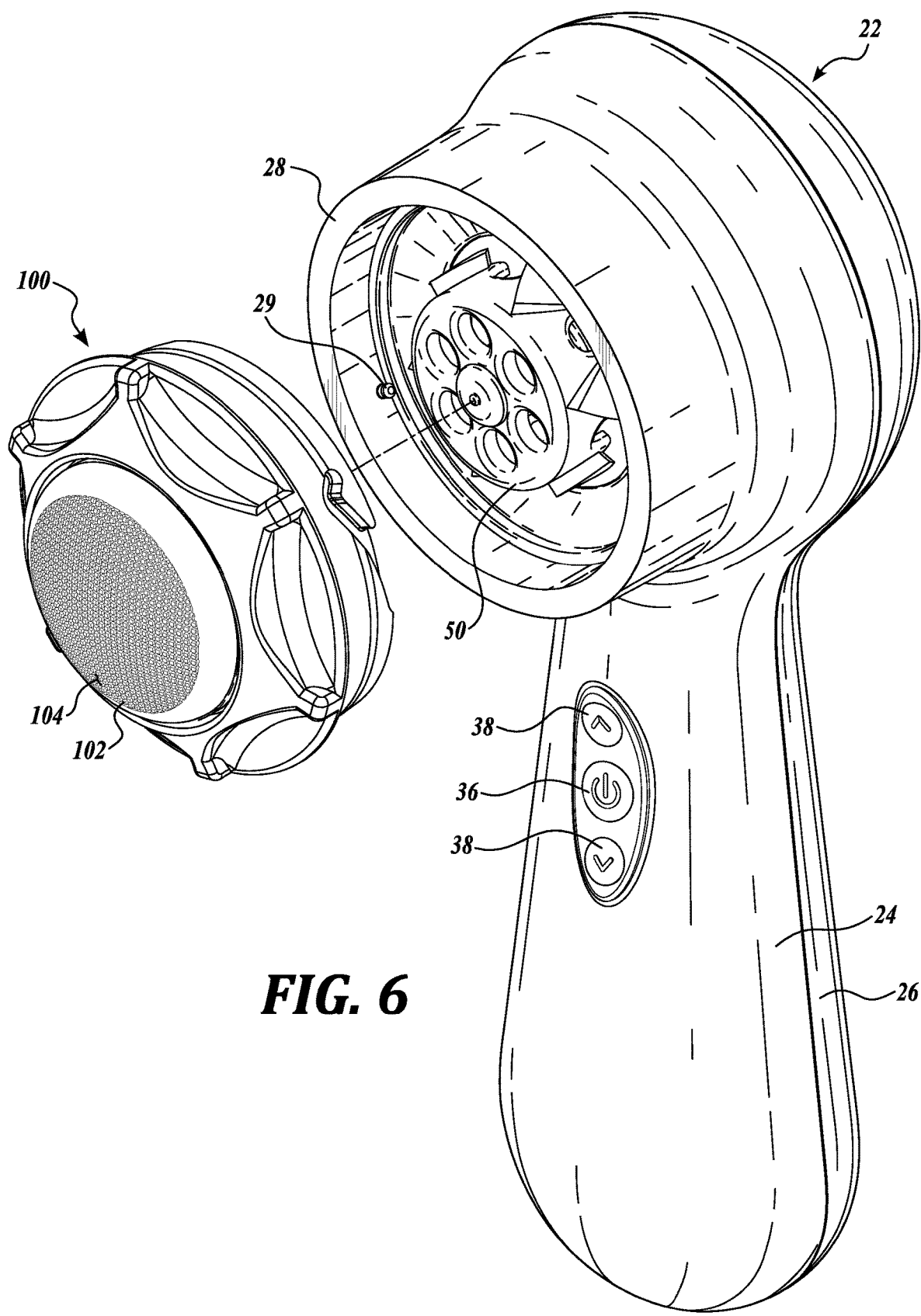
FIG. 6 is a perspective view of a personal care appliance with the cleaning head shown in FIG. 1, with the cleaning head positioned to be attached to the personal care appliance.
Figure 7:
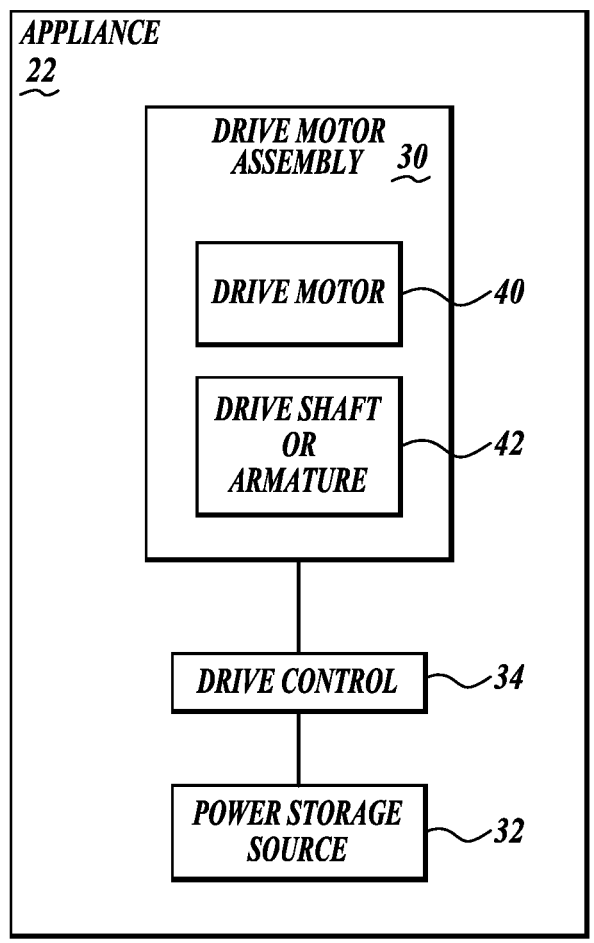
FIG. 7 is a functional block diagram of the personal care appliance shown in FIG. 6.

An exemplary personal care appliance 22 with the cleaning head 100 is illustrated in FIG. 6 and a functional block view of the assembly is shown in FIG. 7. Referring to FIG. 6, the appliance 22 includes a body 24 having a handle portion 26 and a head attachment portion 28. The head attachment portion 28 is configured to selectively attach a head, such as cleaning head 100, to the appliance 22. The appliance body 24 houses the operating structure of the appliance 22, and drivably engages the cleaning head 100 through a drive boss 50 located in the head attachment portion 28. In this embodiment the appliance 22 includes a drive motor assembly 30, a power storage source 32, such as a rechargeable battery, and a drive control circuit 34 (see FIG. 7). An on/off button 36 (see FIG. 6) enables the user to selectively deliver power from the power storage source 32 to the drive motor assembly 30. In some embodiments, the drive control circuit 34 includes one or more power adjust or mode control buttons 38 on the appliance 22 that are configured to provide user control of the drive motor assembly 30, such as a programmed microcontroller or processor, which is configured to control the delivery of power to the drive motor assembly 30. The drive motor assembly 30 in some embodiments includes an electric drive motor 40 that drives an attached head, such as head 100, via a drive shaft or armature 42. The individual components illustrated in FIG. 7 are well known in the art, and therefore will not be further described herein. An example of a drive motor assembly 30 that may be employed by the appliance 22 to oscillate the head 100 is shown and described in U.S. Pat. No. 7,786,626, the disclosure of which is hereby incorporated by reference in its entirety. It will be understood that the particular drive motor assembly is merely an example of the structure and operation of one such appliance and that the structure, operation frequency, and oscillation amplitude of such an appliance could be different depending in part on its intended application and/or characteristics of the head, such as its inertial properties, etc. In some embodiments of the present disclosure, the frequency ranges are selected to drive the attached head at near resonance. Thus, selected frequency ranges are dependent, in part, on the inertial properties of the attached head. It will be appreciated that driving the attached head at near resonance provides many benefits, including the ability to drive the attached head at suitable amplitudes in loaded conditions (e.g., when contacting the skin).

Referring again to FIGS. 1-3, the cleaning head 100 in a current embodiment includes a pliable fluid-filled bladder 102, a housing or bladder support 110 that is fixed to and supports the bladder 102 such that at least a portion of an outward facing micro-engineered surface 104 of the bladder 102 extends beyond the bladder support 110 (FIG. 2), and an annular outer retainer 105 that is configured to receive and retain the bladder support 110. The outer retainer 105 is configured to releasably engage the personal care appliance 22 to removably connect the cleaning head 100 to the appliance 22 (see FIG. 6).

In particular, the cleaning head 100 is configured to be attachable to the personal care appliance 22 such that the appliance 22 selectively drives the cleaning head 100 in a periodic motion. For example, the bladder support 110 may be configured to move along a circular path, oscillate rotationally about an axis perpendicular to the bladder support 110, and/or oscillate linearly, for example, side-to-side and/or vibrate in an in-and-out direction perpendicular to the face of the cleaning head 100. In some embodiments the appliance 22 may include a drive mode to drive the cleaning head 100 in a continuous rotational mode, for example, providing suitable user drive controls 34 on the handle portion 26. In some embodiments the bladder support 110 is, or may be, driven to oscillate at a sonic frequency, which can provide improved control and precision, for example, to facilitate the removal of dirt, dead skin, oils, hair, and the like.

The outer retainer 105 includes a plurality of engagement portions 105A that are configured to attach the cleaning head 100 to corresponding rods or pins 29 in the head attachment portion 28 of the appliance 22 (FIG. 6, one pin 29 visible). A central housing portion or opening 105B of the outer retainer 105 is configured to receive and retain the bladder support 110 and pliable bladder 102 without interfering with oscillatory motion of the bladder support 110, and such that the bladder support 110 is drivably engaged by the appliance 22. In this embodiment the bladder support 110 defines a recess or cavity 101 that is configured to receive and fixedly attach to the bladder 102. The outer retainer 105 and the bladder support 110 in some embodiments are constructed from plastic, such as nylon, polyurethane, polypropylene, polyethylene, etc., although other materials may be utilized, including lightweight metals, such as aluminum, titanium, etc.

In some embodiments the drive motor assembly 30 (FIG. 4) is configured to oscillate the bladder support 110, typically in the range of 90-300 Hz, for example, oscillating the bladder support 110 within an angular range of 8-26 degrees. In some embodiments the bladder support 110 is driven at frequencies between about 100 Hz to 190 Hz with an amplitude or range of about 12-18 degrees. In other embodiments, the bladder support 110 is driven at frequencies of about 168 Hz to 178 Hz, amplitudes of about 12-18 degrees, and a duty cycle of about 36-48%.

Figure 4:
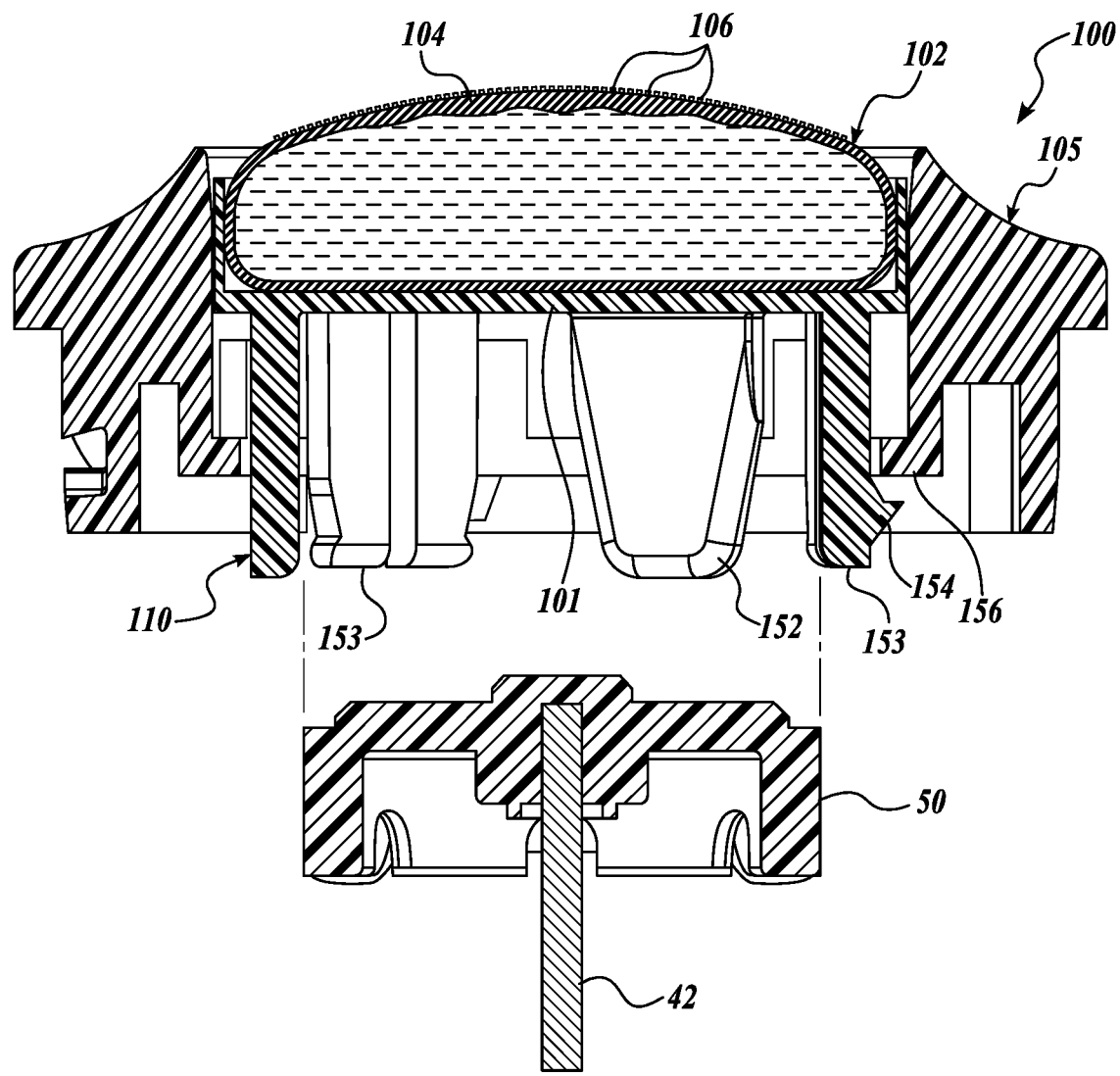
FIG. 4 is a sectional view of the cleaning head through section 4-4 indicated in FIG. 3, and showing an exemplary drive boss for driving the cleaning head.

FIG. 4 is a sectional view of the cleaning head 100 through section 4-4 indicated in FIG. 3. The bladder support 110 includes a plurality of legs 153 that extend below the cavity 101 and includes a projection 154 configured to engage a stop element 156 on the retainer 105, such that the bladder support 110 is releasably retained by the retainer 105 during use. The bladder support 110 is configured to interface directly or indirectly (e.g., via drive boss 50) with the drive shaft or armature 42 of the drive motor assembly 30 at a first or inner end comprising the engagement member 152.

Figure 5:
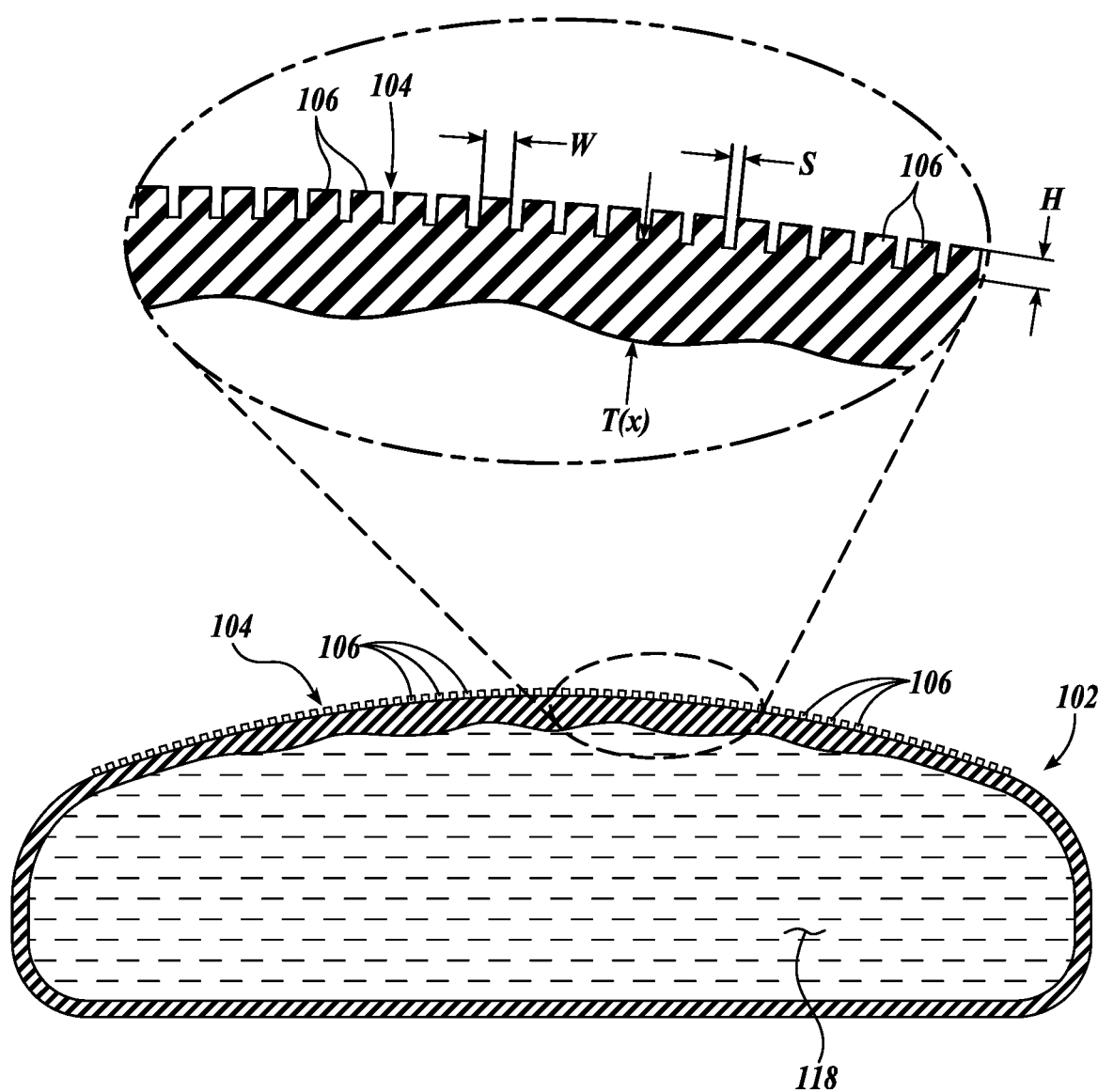
FIG. 5 is a sectional and detail view of the pliable bladder of the cleaning head shown in FIG. 1.

FIG. 5 shows a cross section of the fluid-filled pliable bladder 102 with a detail view showing a portion of the outward facing surface 104. The pliable bladder 102 in a current embodiment is made from one or more natural or synthetic rubbers, for example, silicone rubber. The bladder 102 is filled with a fluid 118, for example, air, water, natural oils, non-Newtonian fluids, or the like. A non-Newtonian fluid is a fluid wherein the viscosity of the fluid depends on the stress applied to the fluid. For example, in some embodiments the fluid 118 is pressurized above atmospheric pressure such that the bladder 102 is maintained in tension by the pressurized fluid 118. For example, the bladder may be pressurized to between 15 and 30 psia, or greater than 30 psia.

At least a portion of the outward facing surface 104 of the bladder 102 includes a plurality of small, closely spaced elastic fingers or projections 106 that are configured to engage the surface of the user's skin. The elastic projections 106 are preferably integrally formed portions of the bladder 102. The bladder 102 has a wall base thickness $T(x)$, wherein the "base thickness" is herein defined as the thickness of the bladder wall not including the projections 106. In some embodiments it is contemplated that the wall base thickness $T(x)$ may be uniform. As illustrated in FIG. 5, in a currently preferred embodiment the wall base thickness $T(x)$ varies. The variable base thickness $T(x)$ is preferably configured to produces a desired non-uniform stiffness/elastic properties of the bladder 102 along at least a portion of the outward facing surface 104. For example, the wall base thickness $T(x)$ may be greater near a center of the bladder 102 to provide a stiffer response to the forces encountered during use, and the thickness may be smaller near the perimeter. In one embodiment the thickness of the bladder 102 is non-uniform along a diameter of the bladder 102, and is constant circumferentially such that the bladder 102 is rotationally symmetric about a central axis of the bladder 102.

Other thickness profiles are contemplated and may be selected to produce a desired action against a user's skin. For example, the thickness may vary periodically, for example sinusoidally, in the radial direction and is uniform circumferentially, to produce annular rings with greater stiffness, separated by lower stiffness rings. It is contemplated that in some embodiments the wall base thickness $T(x)$ may change discontinuously. In other embodiments the wall base thickness $T(X)$ varies circumferentially, and is uniform radially, defining radial, relatively rigid "spokes" along at least the upper surface of the bladder.

The pliable projections 106 extending from the variable thickness wall base are sized, spaced, and shaped such that the projections 106 dynamically bend and elastically deform, causing adjacent projections 106 to interact during use, e.g., such that the projections 106 dynamically contact and move away from neighboring projections 106. During use the projections 106 may therefore be configured such that the projections 106 gently trap, "grab" or otherwise capture particles on (and in) the user's skin, for example, dead skin cells, dirt, makeup, hair follicles, and the like.

In the embodiment shown in FIG. 5 the projections 106 have a generally polygonal cross section, for example, a square cross section with transverse dimensions, or widths W that are between 0.060 inch and 0.125 inch and a height H that may be, for example, between 0.050 inch and 0.080 inch. The projections 106 are closely spaced, for example, a spacing S when at rest between 0.020 inch and 0.060 inch.

Figure 8:
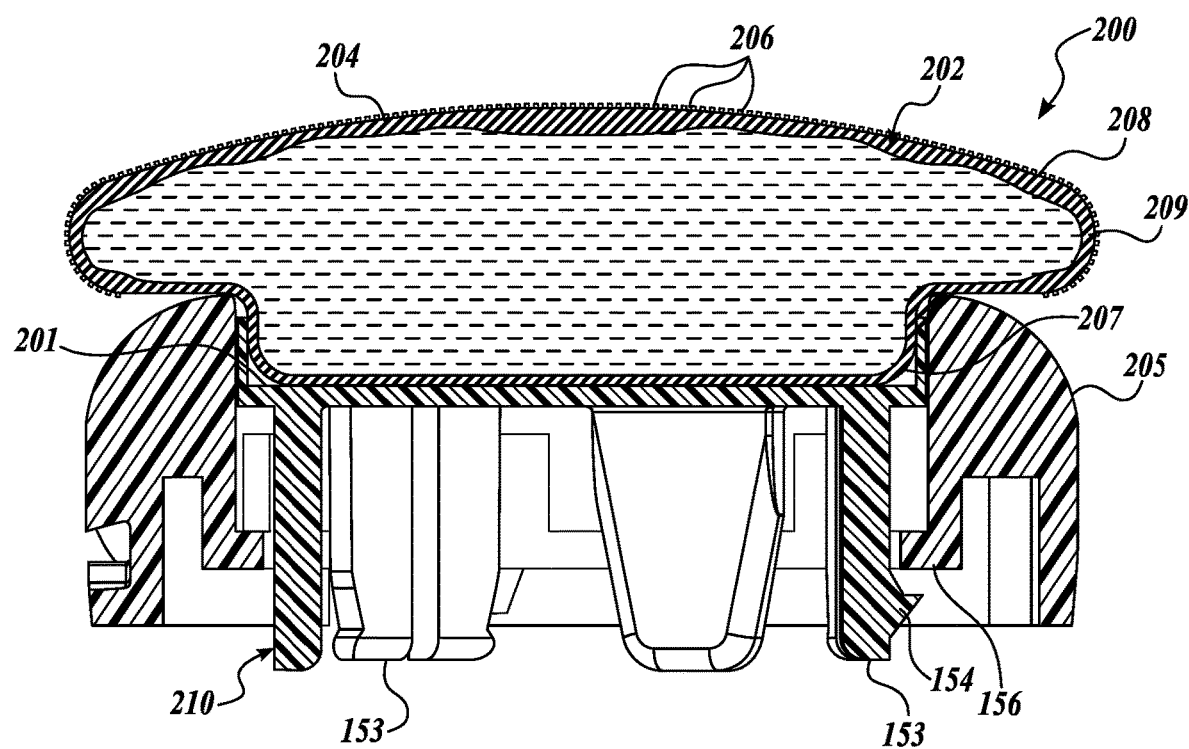
FIG. 8 is a sectional view of another embodiment of a cleaning head in accordance with the present invention.

Another embodiment of a cleaning head 200 in accordance with the present invention is shown in sectional view in FIG. 8. The cleaning head 200 shares many of the features of the cleaning head 100 described above and are contemplated for the cleaning head 200. For brevity and clarity, common features and options described above are not be reiterated, and it is intended that features described for the embodiment described with reference to cleaning head 100 may be provided in cleaning head 200, as far as practicable.

In this embodiment the cleaning head 200 includes a pliable fluid-filled bladder 202 that is fixedly attached to a bladder support 210. The bladder support 210 is removably retained by a retainer 205, and may be otherwise similar to the bladder support 110 discussed above. At least a portion of the outer surface of the fluid-filled bladder 202 defines a surface 204 that includes a plurality of small, closely spaced elastic fingers or projections 206 configured to engage the user's skin. The individual projections 206 may be similar to the projections 106 described above with widths W, height H, spacing S, and the bladder 220 may have a variable base thickness T(x) as discussed above. In this embodiment the bladder 202 includes a narrower central portion 207, e.g., a smaller-diameter central portion 207 that extends into and is fixed in the cavity 201 defined by the bladder support 210, and a wider portion 208 (e.g., larger-diameter portion) that extends from the narrower portion 207 such that the bladder 202 has a generally mushroom shape. The plurality of projections 206 in this embodiment are also provided and cooperatively define the arcuate radially outer surface 209 of the bladder 202. For example, the wider portion 208 may extend to, or beyond, the radially outer perimeter of the outer retainer 205. In a current embodiment the axial dimension, or thickness, of the narrower portion 207 and the axial dimension of the wider portion may be similar, for example within a factor of two, and the diameter or lateral dimension of the narrower portion 207 may be similar to the diameter or lateral dimension of the wider portion 208, for example within a factor of two.

This second embodiment of the cleaning head 200 has certain advantages. The arcuate radially outer surface 209 of the bladder 202, which includes projections 206, is much narrower (e.g., much shorter radius) than the central portion of the bladder 202, which facilitates positioning and maneuvering the bladder 202, and in particular the novel pliable fingers or projections 206 over contoured body regions, including for example around the user's nose and ears. In all cases, it will be appreciated that the closely spaced fingers or projections 206 will, in general, tend to move toward each other when the bladder 202 is in use, because pressing the pliable bladder 202 against the user will naturally deform or urge the bladder 202 locally toward a flatter shape. This deforming action facilitates the projections 206 (adjacent to the skin) coming together to improve the cleaning action of the cleaning head 100, 200.

The detailed description set forth above in connection with the appended drawings, where like numerals reference like elements, are intended as a description of various embodiments of the present disclosure and are not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result.

In the foregoing description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

The present application may include references to directions, such as "forward," "rearward," "front," "back," "upward," "downward," "right hand," "left hand," "lateral," "medial," "in," "out," "extended," "advanced," "retracted," "proximal," "distal," "central," etc. These references, and other similar references in the present application, are only to assist in helping describe and understand the particular embodiment and are not intended to limit the present disclosure to these directions or locations.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The term "about," "approximately," etc., means plus or minus 5% of the stated value.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

While illustrative embodiments have been illustrated and described, it will be appreciated that various changes can be made therein without departing from the spirit and scope of the invention.

The embodiments of the invention in which an exclusive property or privilege is claimed are defined as follows:

1. A cleaning head for a personal care appliance comprising:
    an elastic bladder comprising a bladder wall enclosing a fluid, wherein the bladder wall comprises an inner base portion having a base thickness and a plurality of spaced projections extending outwardly from the inner base portion;
    a bladder support comprising a receiver portion, wherein the elastic bladder is fixedly attached to the receiver portion; and
    a retainer configured to attach the bladder support to the personal care appliance such that the bladder support is drivably engaged by the personal care appliance;
    wherein at least some of the plurality of spaced projections are configured to dynamically engage and disengage with neighboring ones of the plurality of spaced projections during use.

2. The cleaning head of claim 1, wherein the receiver portion of the bladder support comprises an annular wall configured to surround at least a portion of the elastic bladder.

3. The cleaning head of claim 1, wherein the plurality of spaced projections have a polygonal cross section.

4. The cleaning head of claim 1, wherein the plurality of spaced projections have a transverse dimension between 0.060 inch and 0.125 inch.

5. The cleaning head of claim 1, wherein the plurality of spaced projections have a nominal spacing in the range of 0.030 and 0.040 inch between adjacent spaced projections.

6. The cleaning head of claim 1, wherein the elastic bladder comprises a natural or synthetic rubber.

7. The cleaning head of claim 1, wherein the base thickness of the inner base portion is not constant.

8. The cleaning head of claim 1, wherein the fluid in the elastic bladder comprises au.

9. The cleaning head of claim 1, wherein the fluid in the elastic bladder comprises oil or water.

10. The cleaning head of claim 1, wherein the fluid in the elastic bladder is pressurized above atmospheric pressure.

11. The cleaning head of claim 1, wherein the fluid in the elastic bladder is pressurized to at least 30 psi.

12. The cleaning head of claim 1, wherein the elastic bladder comprises a relatively smaller diameter portion that engages the bladder support, and a relatively larger diameter portion extending from the smaller diameter portion.

13. The cleaning head of claim 12, wherein the larger diameter portion defines a narrow circumferential surface, and wherein at least a portion of the plurality of spaced projections extend outwardly from the narrow circumferential surface.

14. The cleaning head of claim 13, wherein the bladder support defines a cavity configured to receive the smaller diameter portion of the elastic bladder, and the larger diameter portion of the elastic bladder extends radially away from the bladder support.

15. The cleaning head of claim 14, wherein the larger diameter portion of the elastic bladder extends radially beyond a radially outer edge of the retainer.

16. A personal care appliance comprising:
a body having a head attachment portion; and
a cleaning head in accordance with claim 1 wherein the cleaning head is configured to releasably engage the head attachment portion.

17. A cleaning head for a personal care appliance comprising: a bladder support comprising a receiver portion defining a cavity;
an elastic bladder having a first portion disposed in the cavity and fixedly attached to the bladder support and a second portion having a non-uniform thickness and a
plurality of spaced projections extending outwardly from the second portion, wherein the elastic bladder encloses a liquid; and
a retainer configured to releasably attach the bladder support to the personal care appliance such that the bladder support is drivably engaged by the personal care appliance;
wherein the elastic bladder is configured to flex during use such that the plurality of spaced projections engage and disengage with neighboring ones of the plurality of spaced projections during use.

18. The cleaning head of claim 17, wherein the plurality of spaced projections have a polygonal cross section and have a nominal spacing in the range of 0.030 and 0.040 inch between adjacent spaced projections.

19. The cleaning head of claim 17, wherein the first portion of the elastic bladder has a smaller transverse dimension than the second portion of the elastic bladder.

20. The cleaning head of claim 19, wherein at least some of the plurality of spaced projections extend radially outwardly from the second portion of the elastic bladder.

* * * * *